United States Patent
Jia et al.

(10) Patent No.: US 9,743,824 B2
(45) Date of Patent: Aug. 29, 2017

(54) ACCURATE AND EFFICIENT POLYP DETECTION IN WIRELESS CAPSULE ENDOSCOPY IMAGES

(71) Applicant: Siemens Medical Solutions USA, Inc., Malvern, PA (US)

(72) Inventors: Jingfei Jia, New York City, NY (US); Shanhui Sun, Plainsboro, NJ (US); Terrence Chen, Princeton, NJ (US); Peng Wang, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 307 days.

(21) Appl. No.: 14/471,143

(22) Filed: Aug. 28, 2014

(65) Prior Publication Data

US 2015/0065850 A1 Mar. 5, 2015

Related U.S. Application Data

(60) Provisional application No. 61/873,412, filed on Sep. 4, 2013.

(51) Int. Cl.
| | |
|---|---|
| *G06K 9/00* | (2006.01) |
| *G06K 9/34* | (2006.01) |
| *A61B 1/00* | (2006.01) |
| *G06T 7/00* | (2017.01) |
| *G06K 9/46* | (2006.01) |
| *A61B 1/04* | (2006.01) |

(52) U.S. Cl.
CPC ........ *A61B 1/00009* (2013.01); *G06K 9/4642* (2013.01); *G06T 7/0012* (2013.01); *A61B 1/041* (2013.01); *G06T 2207/10024* (2013.01); *G06T 2207/10068* (2013.01); *G06T 2207/20081* (2013.01); *G06T 2207/30032* (2013.01)

(58) Field of Classification Search
None
See application file for complete search history.

(56) References Cited

U.S. PATENT DOCUMENTS

| 8,682,142 B1* | 3/2014 | Boskovitz | G11B 27/034 386/278 |
| 2013/0109915 A1* | 5/2013 | Krupnik | G06T 3/4038 600/109 |

OTHER PUBLICATIONS

Ravesteijn et al. "Computer-Aided Detection of Polyps in CT Colonography Using Logistic Regression", IEEE Transactions on Medical Imaging, vol. 29, No. 1, Jan. 2010, pp. 120-131.*
Navneet Dalai, et al., "Histograms of Oriented Gradients for Human Detection," , International Conference on Computer Vision & Pattern Recognition (CVPR '05), 1 (2005), pp. 886-893.
(Continued)

*Primary Examiner* — Randolph I Chu

(57) ABSTRACT

A method for detecting polyps in endoscopy images includes pruning a plurality of two dimensional digitized images received from an endoscopy apparatus to remove images that are unlikely to depict a polyp, where a plurality of candidate images remains that are likely to depict a polyp, pruning non-polyp pixels that are unlikely to be part of a polyp depiction from the candidate images, detecting polyp candidates in the pruned candidate images, extracting features from the polyp candidates, and performing a regression on the extracted features to determine whether the polyp candidate is likely to be an actual polyp.

30 Claims, 6 Drawing Sheets

(56) References Cited

OTHER PUBLICATIONS

Yefeng Zheng, et al., "Four-Chamber Heart Modeling and Automatic Segmentation for 3D Cardiac CT Volumes Using Marginal Space Learning and Steerable Features," IEEE Transaction on Medical Imaging, pp. 1-14, 2008.

Timo Ojala, et al., "Performance Evaluation of Texture Measures With Classification Based on Kullback Discrimination of Distributions," IEEE, pp. 582-585, 1994.

Timo Ojala, et al., "Multiresolution Gray Scale and Rotation Invariant Texture Classification With Local Binary Patterns," Ref: TPAMI 112278, pp. 1-35.

Chih-Chung Chang, et al., "LIBSVM: A Library for Support Vector Machines," pp. 1-39, 2001.

\* cited by examiner

|  | Test1 | Test2 | Test3 |
| --- | --- | --- | --- |
| Original | 0.603 | 0.636 | 0.671 |
| Perturbed | 0.618 | 0.658 | 0.669 |
| Original + Perturbed | 0.617 | 0.657 | 0.669 |

ACCURATE AND EFFICIENT POLYP DETECTION IN WIRELESS CAPSULE ENDOSCOPY IMAGES

CROSS REFERENCE TO RELATED UNITED STATES APPLICATIONS

This application claims priority from "Towards Accurate and Efficient Polyp Detection in Wireless Capsule Endoscopy Images", U.S. Provisional Application No. 61/873,412 of Jia, et al., filed Sep. 4, 2013, the contents of which are herein incorporated by reference in their entirety.

TECHNICAL FIELD

This disclosure is directed to methods and systems for detecting polyps in images acquired through Wireless Capsule Endoscopy.

DISCUSSION OF THE RELATED ART

A polyp is an abnormal growth of tissue protruding from a mucous membrane. Bowel cancer may develop from bowel polyps. Detecting cancers at their early stages by means of polyp diagnosis is important in curing cancers. The Wireless Capsule Endoscopy (WCE) imaging technique can provide a painless and non-invasive way to examine the gastrointestinal tract and can be utilized to detect polyps, and has become well accepted by clinicians and patients. WCE uses a capsule the size and shape of a pill that contains a tiny camera. After a patient swallows the capsule, it takes pictures of the inside of the gastrointestinal tract. The captured images are wirelessly transmitted to an external receiver worn by or near the patient using an appropriate frequency band. The collected images may then be transferred to a computer for diagnosis, review and display. A WCE video of a single gastrointestinal tract exam can contain up to 50,000-60,000 2-dimensional images. Manually inspecting such a significant number of WCE images is tedious, error prone, and represents a burden for clinicians. Accurate and fast computer-aided polyp detection algorithms is useful. However, due to non-uniform illumination from the light emitting diodes in the capsule, disturbances such as bubbles and trash liquids, the complexity of the anatomy inside the bowel, and large variations in the size and shape and size of the polyps, accurate polyp detection from WCE images is a challenging task. WCE is a new field of research, and thus few papers have been published that deal with polyp detection in WCE images.

SUMMARY

Exemplary embodiments of the disclosure as described herein are directed to new polyp detection methods for Wireless Capsule Endoscopy (WCE) images. A method according to an embodiment of the disclosure includes the steps of greenish image pruning, pixel-wise pruning, initial polyp candidate localization and a regression based polyp detection. Methods according to embodiments of the disclosure were validated using three groups of 2-fold cross validation on 27984 images. On average, a 0.648 true positive rate was achieved with a 0.1 false positive rate. A detection process according to an embodiment of the disclosure executed in 0.83 seconds per image on average.

According to an embodiment of the disclosure, there is provided a method for detecting polyps in endoscopy images, including pruning a plurality of two dimensional digitized images received from an endoscopy apparatus to remove images that are unlikely to depict a polyp, where a plurality of candidate images remains that are likely to depict a polyp, pruning non-polyp pixels that are unlikely to be part of a polyp depiction from the candidate images, detecting polyp candidates in the pruned candidate images, extracting features from the polyp candidates, and performing a regression on the extracted features to determine whether the polyp candidate is likely to be an actual polyp.

According to a further aspect of the disclosure, pruning non-polyp pixels from the candidate images comprises calculating a posterior Bayesian probability of a pixel i being a polyp pixel $$g(x_i) \equiv P(x_i \text{ is } polyp) = \frac{P(polyp)f_P(x_i)}{P(polyp)f_P(x_i) + P(\text{normal})f_N(x_i)},$$

where $x_i$ is an $N_c$ dimensional vector associated with pixel i that includes intensity values from different color spaces, P(polyp) and P(normal) denote the prior probability that pixel i is a polyp pixel or a non-polyp pixel respectively, and $f_P$ and $f_N$ are distribution functions with respect to $x_i$, given that pixel i is either polyp or non-polyp, respectively, where if $g(x_i)$ is less than a predetermined threshold, pixel i is determined to be a non-polyp pixel.

According to a further aspect of the disclosure, $N_c=3$ is a number of color channels, the color channels are (BUH), where B is selected from an RGB color space, U is selected from a LUV color space, and H is selected from a HSV color space.

According to a further aspect of the disclosure, $g(x_i)$ is approximated by $$\frac{f_P(x_i)}{f_N(x_i)}.$$

According to a further aspect of the disclosure, polyp candidates for an image $I_k$ comprise a plurality of ellipses $\{(E_k^l, p_k^l)\}_{l=1}^{N_k}$ for each image $I_k$, where ellipse $E_k^l$ is a polyp region-of-interest with a polyp probability $p_k^l$ and $N_k$ is the number of ellipses for image $I_k$.

According to a further aspect of the disclosure, features extracted from the polyp candidates include geometric features and appearance based features, where the geometric features include an area of each ellipse, and a ratio of the major axis length and the minor axis length of each ellipse, and where the appearance based features are extracted from 3 concentric regions-of-interest (ROIs) about the detected ellipse.

According to a further aspect of the disclosure, appearance based features include a multi-scaled rotational invariant local binary pattern where each of a plurality of circular neighbors of a pixel i are labeled as 1 if the intensity of the neighbor is greater than that of pixel i, and 0 otherwise, and a binary number formed by the values of the plurality of neighbors is to classified into a bin based on a number of consecutive 1's and consecutive 0's in each binary number, where the binary number is classified into a separate bin if there are no consecutive 1's and consecutive 0's in the binary number, where each bin is a feature.

According to a further aspect of the disclosure, appearance based features include a histogram of oriented gradients (HOG) calculated by computing image gradients inside each ROI, and assigning a magnitude of each gradient to a direction bin based on an orientation of each polyp candidate ellipse.

According to a further aspect of the disclosure, appearance based features further include calculating a dissimilarity of HOG features between two ROIs from $d(f,g) = \sum_{i=1}^{N}|f_i-g_i|$, where f and g are HOG histograms for the two regions, respectively, $\|\cdot\|$ is an $L_I$ norm, and N is a number of direction bins, and calculating a color distribution dissimilarity between two regions from $d(f,g)=\sum_{i=1}^{N}|f_i-g_i|$, where f and g are intensity distribution histograms for the two regions, respectively, for each color.

According to a further aspect of the disclosure, performing a regression on the extracted features comprises solving $Y \approx f(X, \beta)$, where Y is a target variable, X is a vector of the extracted features, and $\beta$ are predetermined parameters calculated during a training stage, where target value $y_k^l$ for the l-th polyp candidate of image $I_k$ is defined as an overlap ratio between the ellipse $E_k^l$ of the polyp candidate and a ground truth ellipse $E_k^g$ $$y_k^l = \begin{cases} \min\left(\frac{|E_k^g \cap E_k^l|}{|E_k^g|}, \frac{|E_k^g \cap E_k^l|}{|E_k^l|}\right) & I_k \text{ is positive image} \\ 0 & I_k \text{ is negative image} \end{cases},$$

where $\|\cdot\|$ represents an area of the argument ellipse.

According to a further aspect of the disclosure, $f(X, \beta)$ is a support vector regressor.

According to a further aspect of the disclosure, the method includes calculating an image-wise polyp score $S_k$ that represents a likelihood that an image $I_k$ contains one or more polyps from $S_k = \sum_{l=1}^{\tilde{N}_k}(w \cdot p_k^l + (1-w) \cdot y_k^l)$, where $p_k^l$ is the probability of candidate ellipse $E_k^l$ being a polyp where $\{p_k^l\}_{l=1}^{N_k}$ is sorted in descending order and a top $\tilde{N}_k$ detected polyp candidates are selected, $y_k^l$ is the corresponding regression target value, and w is a combining weight determined in a training stage to achieve a largest true positive rate at a predetermined false positive rate.

According to another embodiment of the disclosure, there is provided a method for training a detector that detects polyps in endoscopy images that includes detecting polyp candidates in a plurality of two dimensional digitized images received from an endoscopy apparatus, where polyp candidates for an image $I_k$ comprise a plurality of ellipses $\{(E_k^l, p_k^l)\}_{l=1}^{n_k}$ for each image $I_k$, where ellipse $E_k^l$ is a polyp region-of-interest with a polyp probability $p_k^l$ and $N_k$ is the number of ellipses for image $I_k$, extracting features from the polyp candidates, calculating target values Y for a regression model represented by $Y \approx f(X, \beta)$, where X is a vector of features, and $\beta$ are unknown parameters to be determined, and determining the parameters $\beta$ for the regression model from the target values Y and feature vector X.

According to a further aspect of the disclosure, target value $y_k^l$ for the l-th polyp candidate of image $I_k$ is defined as an overlap ratio between the ellipse $E_k^l$ of the polyp candidate and a ground truth ellipse $E_k^g$ $$y_k^l = \begin{cases} \min\left(\frac{|E_k^g \cap E_k^l|}{|E_k^g|}, \frac{|E_k^g \cap E_k^l|}{|E_k^l|}\right) & I_k \text{ is positive image} \\ 0 & I_k \text{ is negative image} \end{cases},$$

where $\|\cdot\|$ represents an area of the argument ellipse.

According to a further aspect of the disclosure, features extracted from the polyp candidates include geometric features and appearance based features, where the geometric features include an area of each ellipse, and a ratio of the major axis length and the minor axis length of each ellipse, and where the appearance based features are extracted from 3 concentric regions-of-interest (ROIs) about the detected ellipse.

According to a further aspect of the disclosure, appearance based features include a multi-scaled rotational invariant local binary pattern where each of a plurality of circular neighbors of a pixel i are labeled as 1 if the intensity if the neighbor is greater than that of pixel i, and 0 otherwise, and a binary number formed by the values of the plurality of neighbors is classified into a bin based on a number of consecutive 1's and consecutive 0's in each binary number, where the binary number is classified into a separate bin if there are no consecutive 1's and consecutive 0's in the binary number, where each bin is a feature.

According to a further aspect of the disclosure, appearance based features include a histogram of oriented gradients (HOG) calculated by computing image gradients inside each ROI, and assigning a magnitude of each gradient to a direction bin based on an orientation of each polyp candidate ellipse.

According to a further aspect of the disclosure, appearance based features further include calculating a dissimilarity of HOG features between two ROIs from $d(f,g) = \sum_{i=1}^{N}|f_i-g_i|$, where f and g are HOG histograms for the two regions, respectively, $\|\cdot\|$ is an $L_1$ norm, and N is a number of direction bins, and calculating a color distribution dissimilarity between two regions from $d(f,g)=\sum_{i=1}^{N}|f_i-g_i|$, where f and g are intensity distribution histograms for the two regions, respectively, for each color.

According to another embodiment of the disclosure, there is provided a non-transitory program storage device readable by a computer, tangibly embodying a program of instructions executed by the computer to perform the method steps for detecting polyps in endoscopy images.

DETAILED DESCRIPTION OF EXEMPLARY EMBODIMENTS

Figure 1A:
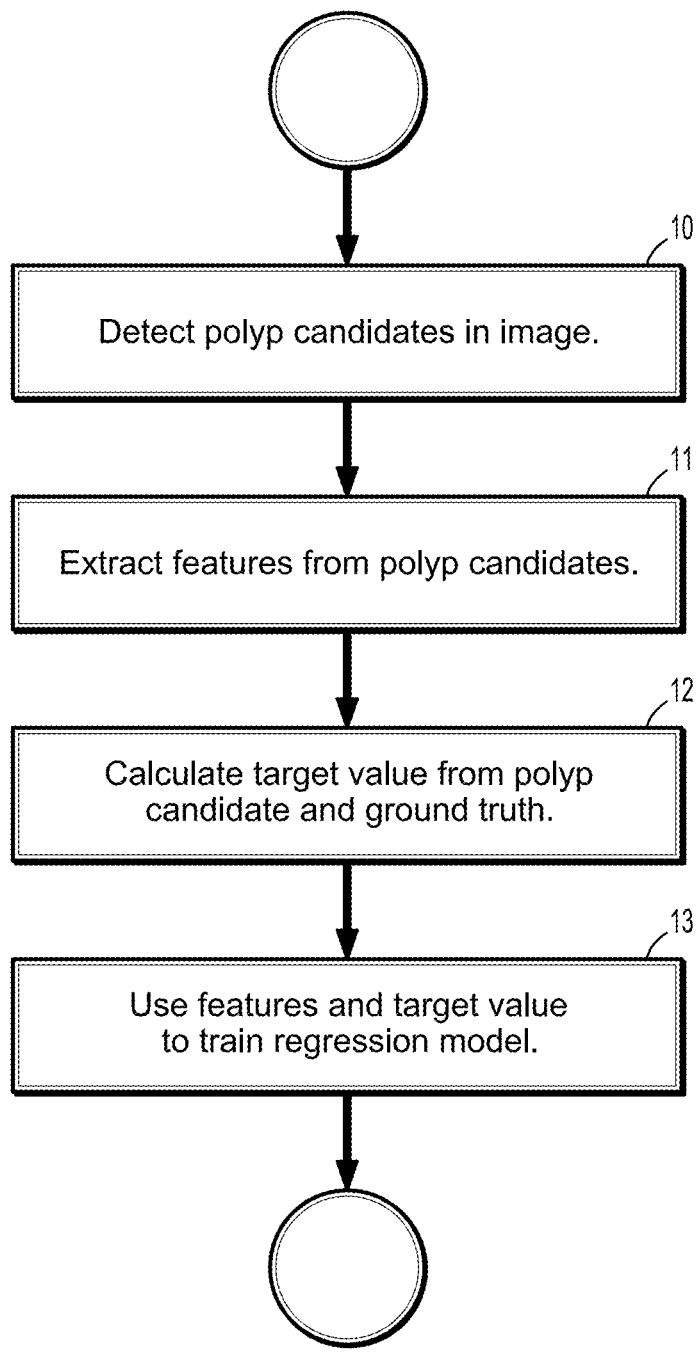
FIGS. 1(a)-(b) are flowcharts of a training procedure and a testing procedure, respectively, according to embodiments of the disclosure.

Exemplary embodiments of the disclosure as described herein generally include systems and methods for detecting polyps in Wireless Capsule Endoscopy (WCE) images.

Accordingly, while the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, methods of embodiments of the disclosure are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Exemplary embodiments of the present disclosure are directed to a novel machine learning based approach to quickly and accurately discriminate a WCE image into a positive, polyp image or a negative, normal image. An algorithm according to an embodiment of the disclosure first removes images that unlikely to contain polyps. Then, hypotheses regarding the position, orientation and scale of the polyps are defined for a polyp-like region-of-interest (ROI) detection, and then a regression based approach is used to validate these hypotheses and determine whether the ROI is a polyp or normal tissue.

A method according to an embodiment of the disclosure can discriminate a polyp image and a normal image. A detection pipeline according to an embodiment of the disclosure may include four components: image-wise pruning, pixel-wise pruning, polyp candidate detection, and regression-based polyp candidate refinement. Image-wise pruning is used to find greenish images, which are unlikely to be polyp images. Pixel-wise pruning is to remove negative pixels and preserve a sufficient number of positive pixels. A result mask corresponding to the positive pixels is provided to a candidate detection stage. According to an embodiment of the disclosure, candidate detection is performed to locate polyp candidate positions, orientations and scale. An exemplary, non-limiting method for detecting polyp candidates comprises Marginal Space Learning. As a result, a set of ellipses $\{(E_k^l, p_k^l)\}_{l=1}^{N_k}$ is generated for each image $I_k$, where $E_k^l$ is a polyp region-of-interest (ROI) with a polyp probability $p_k^l$ and $N_k$ is the number of ellipses generated for image $I_k$. Based on the polyp candidates, a regressor according to an embodiment of the disclosure, such as Support Vector Regression (SVR), can be utilized to differentiate polyp and non-polyp images.

Methods according to embodiments of the disclosure include methods for pixel-wise pruning and methods for regression-based polyp detection, although experiments validated four components in one pipeline. As machine learning based approaches, methods according to embodiments of the disclosure include training and testing stages.

Figure 1B:
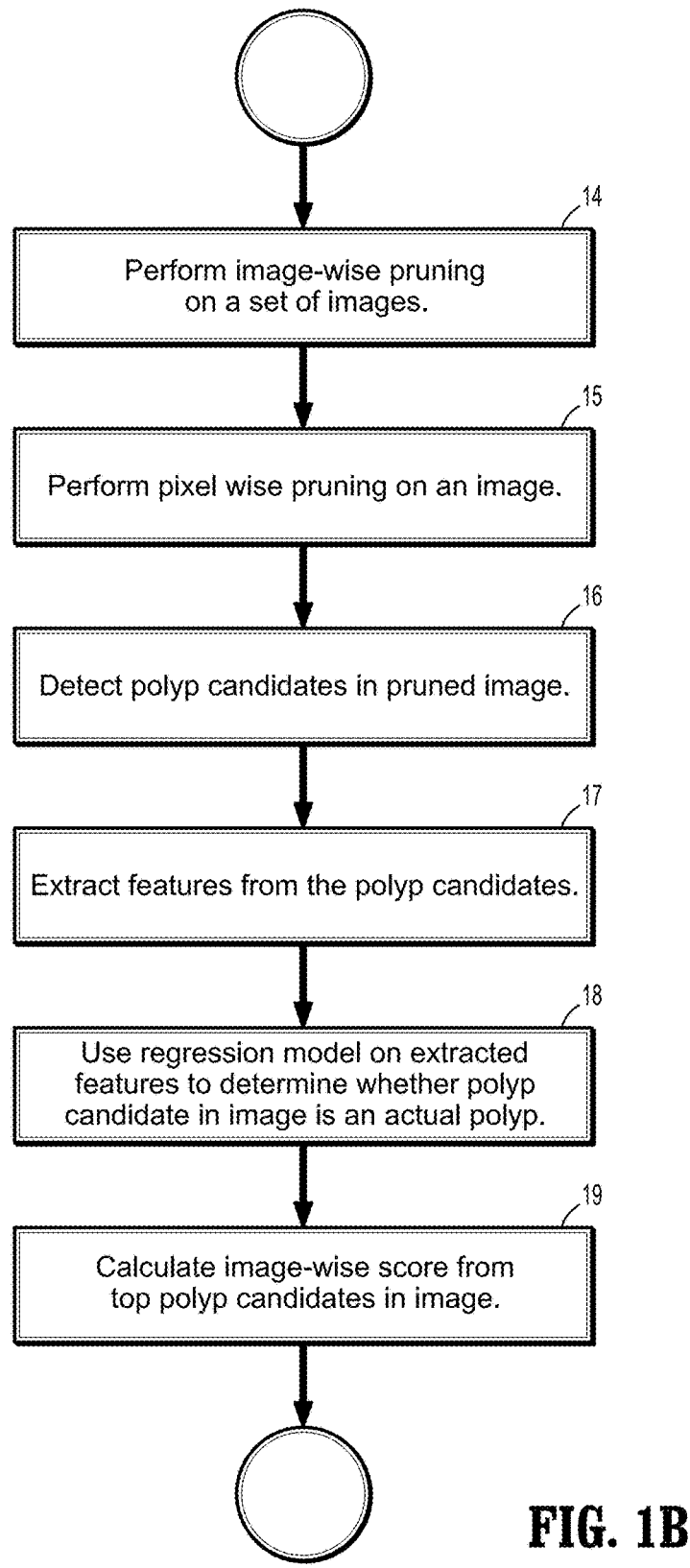

FIGS. 1(a)-(b) are flowcharts of an overview of a training procedure and a testing procedure, respectively, according to embodiments of the disclosure. Referring now to FIG. 1A, given a set of 2-dimensional training images that are known to depict polyps, a training process according to an embodiment of the disclosure begins at step 10 by detecting polyp candidates in each image. Then, for each image, features are extracted from the polyp candidates and ground truth polyps at step 11, and a target value for a regression model is calculated from the polyp candidates and ground truth polyps at step 12. The extracted features and the target values are used to train a regression model at step 13. An exemplary, non-limiting regression model is support vector regression.

Referring now to FIG. 1B, given a set of 2-dimensional testing images received from an endoscopy apparatus, a testing process according to an embodiment of the disclosure begins at step 14 by performing image-wise pruning on the set of images. Image-wise pruning involves pruning or removing those images from the image set that are unlikely to contain polyps, such as images that are primarily green in color. The SVM classifier trained in the training phase is used to predict greenish images. Histograms for the three R, G and B color channels over the whole image are calculated and are utilized as features by the SVM classifier. According to an embodiment of the disclosure, 16 bins are used for each color, for a total of 48 features. The SVM classifier returns a score based on the features, on which the pruning decision is based. Pixel-wise pruning is performed for each image at step 15, which involves pruning or removing non-polyp pixels from the image. A result mask corresponding to the positive pixels is provided to a candidate detection stage. Then, at step 16, polyp candidates are detected in the pruned image to locate polyp candidate positions, orientations and scale, and features are extracted from the polyp candidates at step 17. An exemplary, non-limiting method for detecting polyp candidates comprises Marginal Space Learning. Marginal Space Learning is disclosed in Zheng, et al., "Four-Chamber Heart Modeling And Automatic Segmentation For 3-D Cardiac CT Volumes Using Marginal Space Learning And Steerable Features", Medical Imaging, IEEE Transactions on, 27(11) (2008), 1668-1681, the contents of which are herein incorporated by reference in their entirety. As a result, a set of ellipses $\{(E_k^l, p_k^l)\}_{l=1}^{N_k}$ is generated for each image $I_k$, where $E_k^l$ is a polyp region-of-interest (ROI) with a polyp probability $p_k^l$ and $N_k$ is the number of ellipses generated for image $I_k$. The extracted features are used with the regression model trained by the method of FIG. 1A to determine whether a polyp candidate is an actual polyp, at step 18, and, at step 19, an image-wise score is calculated for each image from the top polyp candidates in that image. Details of the above steps are provided hereinbelow.

In practice, the normal images outnumber the positive images. A significantly unbalanced number of positive and negative images can make the training and testing challenging. According to an embodiment of the disclosure, to deal with this situation, positive images are perturbed by rotation and reflection with respect to the image center. For example, in one experiment of an embodiment of the disclosure, there were 541 positive images and 15000 negative images. According to an embodiment of the disclosure, 12 rotation angles, $\{-10°, -5°, 0°, 5°, 10°, 45°, 90°, 135°, 180°, 225°, 270°, 315°\}$ are used. Note that this number is exemplary and non-limiting, and any number of rotation angles can be used. With reflection, 24 positive samples, including the original image, may be created. According to an embodiment of the disclosure, interpolation may be used to perturb the mages. However, interpolation blurs images. It is also known that some image descriptors, such as a Histogram of Oriented Gradients (HOG), are sensitive to smoothed images. Thus, according to an embodiment of the disclosure, to reduce the bias caused by smoothed perturbed positive images in the training process, every trained normal image is also randomly perturbed to one of those 24 positions. According to an embodiment of the disclosure, bilinear interpolation may provide a balanced solution for image perturbation.

Pixel-Wise Pruning

According to an embodiment of the disclosure, pixel-wise pruning may be performed for the following reasons. (1) The fewer number of processed pixels, the more computationally efficient is the polyp candidate detection. (2) The likelihood of polyp ROIs being detected can be improved if a large number of normal pixels are removed and sufficient number of polyp pixels are preserved.

According to an embodiment of the disclosure, to conduct pixel-wise pruning, a Bayesian decision based method may be used. The posterior probability of a pixel being a polyp pixel i is:

$$g(x_i) \equiv P(x_i \text{ is } polyp) = \frac{P(polyp)f_P(x_i)}{P(polyp)f_P(x_i) + P(normal)f_N(x_i)}, \quad (1)$$

where $x_i$ is a vector with $N_c$ dimensions at pixel i that includes intensity values from different to color spaces. According to an embodiment of the disclosure, $N_c$ is 3. P(polyp) and P(normal) denote the prior probability and $f_P$ and $f_N$ are the distribution functions with respect to $x_i$, given that pixel is either polyp or normal respectively. In a testing stage according to an embodiment of the disclosure, if $g(x_i) < t_p$, the pixel may be labeled as normal, where $t_p$ is a heuristic threshold determined from the training data.

$f_P$ and $f_N$ may be described using a 32×32×32 histogram, which may be learned from the training set. According to an embodiment of the disclosure, an approximation version $$\hat{g}(x) \equiv \frac{f_P(x)}{f_N(x)},$$

is used instead of g(x) to simplify the calculations. According to an embodiment of the disclosure, $t_p$ may be determined based on a criterion that the ratio of removed/preserved polyp pixels on the training set is between 0.01 and 0.05.

To determine the $N_c$=3 color channels, experiments were conducted on three color spaces (RGB, LUV, HSV) as well as a mixture from these three color spaces. For mixed channels, one channel was selected from each color space which discriminates the polyp pixels and non-polyp pixels most effectively. According to an embodiment of the disclosure, R or B were selected from RGB (Red, Green, Blue), as it was found that R and B have similar performance, U was selected from LUV (Luminance, where U and V are chromaticites), and H was selected from HSV (Hue, Saturation, Value). Finally, 5 combinations, RGB, LUV, HSV, BUH and RUH, were compared. From these comparisons, three channels, namely BUH, were selected as providing a best performance for pixel based pruning.

Regression-Based Polyp Detection

According to an embodiment of the disclosure, the following regression analysis may be used to discriminate polyp and normal tissue:

$$Y \approx f(X, \beta) \quad (2)$$

where Y is the target variable, X is the feature vector, and $\beta$ are unknown parameters need be determined in the training stage. Consider a set of sample points, $\{(x_1, y_1), \ldots, (x_l, y_l)\}$, where $x_i \in R^n$ is a feature vector and $y_i \in R^1$ is a target value. According to an embodiment of the disclosure, support vector regression (SVR) may be used as a regressor. An exemplary, non-limiting software package for performing SVR is LIBSVM.

Target Variable: Assume there is a polyp candidate ROI $E_k^l$ and also a ground truth $E_k^g$ for image $I_k$. The target value $y_k^l$ for the l-th polyp candidate of image $I_k$ is defined as an overlap ratio between the candidate ROI and ground truth:

$$y_k^l = \begin{cases} \min\left(\frac{|E_k^g \cap E_k^l|}{|E_k^g|}, \frac{|E_k^g \cap E_k^l|}{|E_k^l|}\right) & I_k \text{ is positive image} \\ 0 & I_k \text{ is negative image} \end{cases} \quad (3)$$

where || refers to the area of a ROI. Note that a subset of candidates are used for training samples. An exemplary, non-limiting number of training samples is 100,000. According to an embodiment of the disclosure, a sampling criterion is to balance the number of negative and positive candidates. In addition, all positive ground truths are used as training samples, whose target values are set to 1.0.

Figure 2:
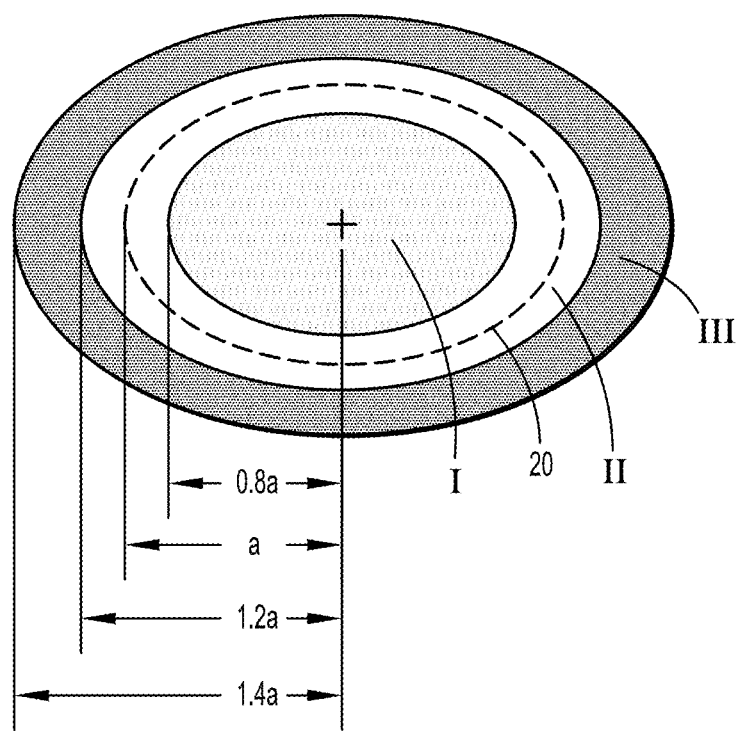
FIG. 2 illustrates the polyp ROIs I, II and III, according to an embodiment of the disclosure.

Feature Extraction: According to an embodiment of the disclosure, both geometric and appearance based discriminative features were used for each polyp candidate. The geometric-based features are defined as follows: the area and the ratio of the major and minor axis lengths of a detected ROI. To extract appearance-based features, three concentric ROIs, denoted as I, II and III are created from a detected ROI. Exemplary, non-limiting scales of these three regions are {0.8; 1.2; 1.4} compared to the size of a detected polyp candidate. FIG. 2 illustrates the polyp ROIs I, II and III. The dashed curve 20 indicates the candidate detection result, and a represents the scale of the candidate detection result. The idea behind these divisions is that I indicates that polyp tissue is more likely in this region, III is more likely to be normal tissue and II indicates an ambiguous boundary region. According to an embodiment of the disclosure, three types of appearance-based features will be described in detail: a multi-scaled Rotation Invariant Local Binary Pattern (RI-LBP), a Histogram of Oriented Gradients (HOG), and Color Distribution Dissimilarity.

Figure 3:
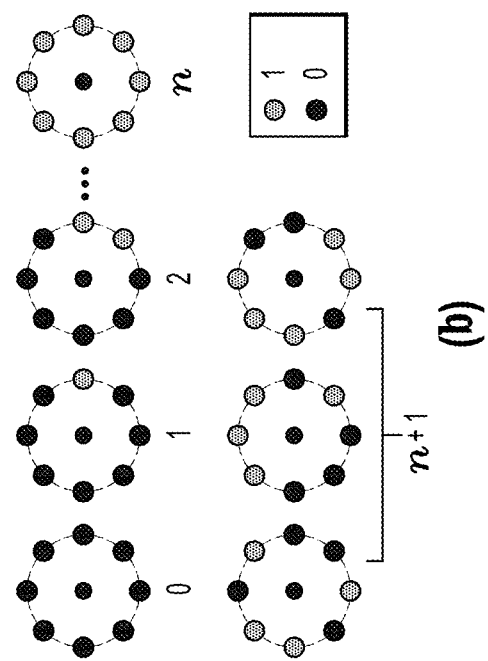
FIGS. 3(a)-(b) illustrate a standard LBP, and an RI-LBP, according to an embodiment of the disclosure.
Figure 3:
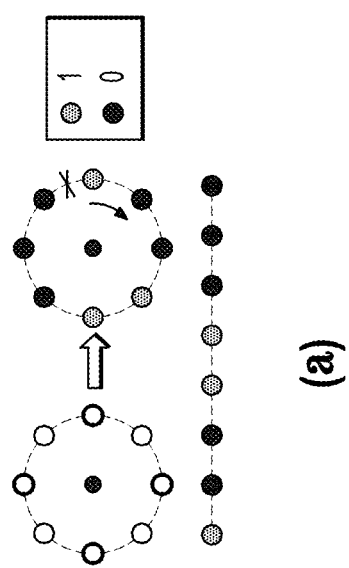

(1) Multi-Scaled RI-LBP Based Features: FIGS. 3(a)-(b) illustrate examples of two LBP definitions. FIG. 3(a) illustrates a standard LBP, and FIG. 3(b) illustrates an RI-LBP. In FIGS. 3(a)-(b), gray dots represent 1, and black dots represent 0. As depicted in FIG. 3(a), $N_1$ circular neighbors of each pixel i in a ROI with a radius r are considered. Each neighbor has a label. A neighbor is labeled as 1 if its value v is greater than i's, otherwise it is labeled as 0. The value v can be a gray value or an intensity value from a different colorspace. An $N_l$-bit binary number, counting from 0° in a clockwise direction, is converted to a decimal number. In the example of FIG. 3(a), the binary number 10011000 is converted to its decimal equivalent, 152. A histogram of all decimal numbers in the ROI is calculated. The normalized histogram bin represents a specific local pattern, which can be utilized as a feature.

FIG. 3(b) illustrates a rotational invariant LBP (RI-LBP) algorithm, which can also reduce the dimensionality of the features. Instead of being converted to a decimal number, the binary number is classified into $N_l+2$ categories ($\{0, \ldots, N_l+1\}$). If the binary number has nonconsecutive 1s and non-consecutive 0s, then it is classified into the category $N_l+1$, otherwise it is classified into one of the other k categories, ($0 \leq k \leq N_l$) in terms of either of the following criteria:

(1) The binary number has k consecutive 1s and $N_l$-k 0s;
(2) The binary number has $N_l$-k consecutive 0s and k 1s.

Then a histogram with $N_l+2$ bins is computed by counting the occurrence frequency of each category. In FIG. 3(b), the upper row depicts, from left to right, the representations of numbers 0, 1, 2, ..., n, and the lower row representations of binary numbers classified into category $N_l+2$.

According to an embodiment of the disclosure, an RI-LBP method is applied in the regions I, II and III individually. Moreover, a multi-scaled method is used with pixel radii of r={1, 3, 5} pixels. An exemplary, non-limiting value of $N_l$ is 8. Thus, an RI-LBP-based histogram of 90 bins is used, in which each bin is a feature.

Figures 4, 5:
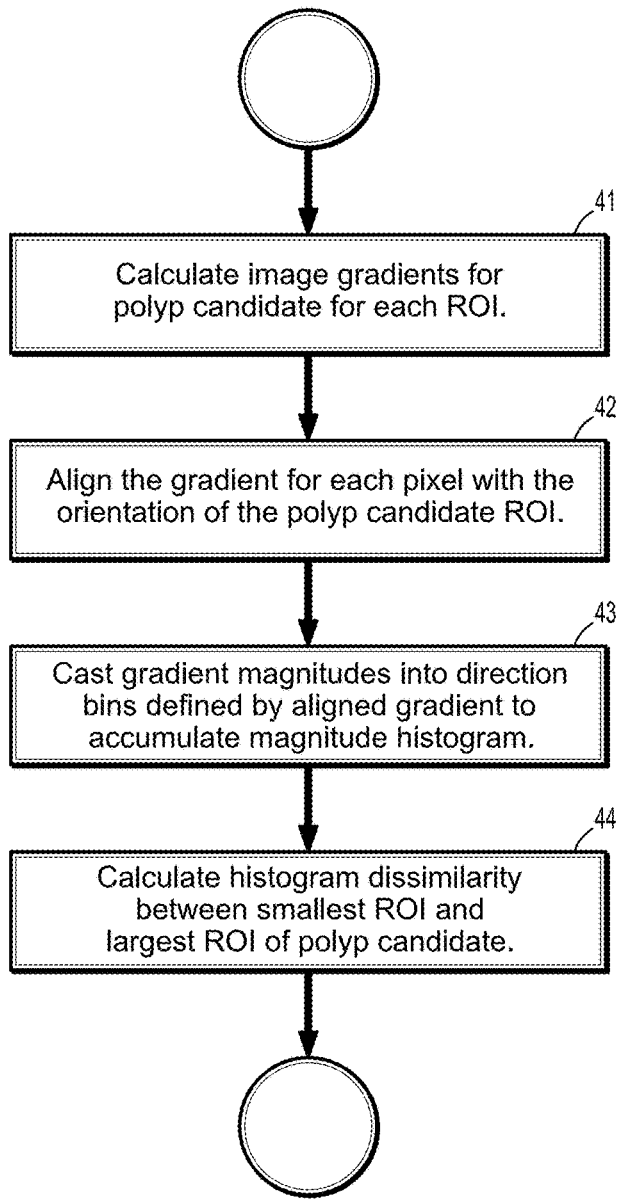
FIG. 4 is a flowchart of a method of calculating HOG features for a polyp candidate, according to an embodiment of the disclosure.
FIG. 5 is a table of summary results of the cross validation performance tests on the original positive images, perturbed images, and combined images, according to an embodiment of the disclosure.

(2) HOG Based Features: HOG features represent a weighted distribution of the gradient orientations in a local region. A flowchart of a method of calculating HOG features for to a polyp candidate is presented in FIG. 4. Referring now to the figure, for a polyp candidate $E_k^i$, image gradients are computed inside the ROIs I, II and III at step 41, using kernels (−1, 0, 1) in the x-direction and $(-1, 0, 1)^T$ in the y-direction. Let $g_i$ and $m_i$ denote gradient direction and magnitude of a pixel i respectively. Then at step 42, $g_i$ is aligned to the orientation of $E_k^i$. Since the polyp has a direction, the gradient direction should be calculated based on polyp direction, which will change the gradient direction to be aligned with the polyp direction. Let $\tilde{g}_i$ represent the aligned gradient direction. Inside each ROI, $m_i$ is cast to the $N_h$ direction bins at step 43, which are uniformly divided between 0° and 180° based on $\tilde{g}_i$, to obtain a magnitude histogram with $N_h$ bins for each ROI. The histograms are normalized over these ROIs. The normalized histograms represent HOG features according to an embodiment of the disclosure.

In addition, the dissimilarity of HOG features of region I (polyp tissue) and III (normal tissue) is computed at step 44. The dissimilarity is defined as follows:

$$d(f,g) = \Sigma_{i=1}^{N} |f_i - g_i| \qquad (4)$$

where f and g are two histograms for regions I and III, respectively, $\|\cdot\|$ is an $L_1$ norm, and $\{f_i\}_{i=1}^{N}$ and $\{g_i\}_{i=1}^{N}$ are the histogram representations. For a HOG based dissimilarity, $N=N_h$. An exemplary, non-limiting value of $N_h$ is 6. According to an embodiment of the disclosure, three RGB channels were used to compute the HOG based features. Thus, 54 HOG features and 3 dissimilarity features are used.

(3) Color Distribution Dissimilarity: Polyp and normal tissues have different intensity distribution in different RGB channels. For example, greener pixels are more likely to be residues while redder pixels are more likely to belong to polyp tissue. According to an embodiment of the disclosure, the color distribution dissimilarity between two ROI regions is given by EQ. (4), where $\{f_i\}_{i=1}^{N}$ and $\{g_i\}_{i=1}^{N}$ are the intensity distribution histograms for between the two regions, respectively. Exemplary, non-limiting choice for the regions are I and III. An exemplary, non-limiting number of bins N is 16, and three RGB channels were used to achieve 3 color distribution dissimilarity features.

Image-Wise Polyp Score

According to an embodiment of the disclosure, an image-wise polyp score $S_k$ represents the likelihood that an image $I_k$ contains one or more polyps. According to an embodiment of the disclosure, $S_k$ may be defined as follows:

$$S_k = \Sigma_{i=1}^{\tilde{N}_k}(w \cdot p_k^i + (1-w) \cdot y_k^i), \qquad (5)$$

where $p_k^i$ is the probability of a candidate $E_k^i$ being polyp, $\{p_k^i\}_{i=1}^{\tilde{N}_k}$ is sorted in descending order, where the top $\tilde{N}_k$ detected polyp candidates are utilized, $y_k^i$ is the corresponding regression target value, and w is a combining weight. An exemplary, non-limiting value of $\tilde{N}_k$ is 30. According to an embodiment of the disclosure, w is optimized in the training stage to achieve the largest true positive rate (TPR or sensitivity) at a predetermined false positive rate (FPR, or 1-specificity). An exemplary, non-limiting value for the predetermined false positive rate is 0.1. TPR and FPR are defined as follows:

$$TPR = \frac{\text{number of true positives}}{\text{number of true positives} + \text{number of false positives}}, \qquad (6)$$

$$FPR = \frac{\text{number of false positives}}{\text{number of true positives} + \text{number of false positives}}. \qquad (7)$$

Experiments

According to an embodiment of the disclosure, a 2-fold cross validation was conducted on 12984 positive images (541 original images+12443 perturbed images) and 15000 negative images. Note that tests were only performed on non-perturbed negative images. The image size was 256×256. For each fold, images were randomly assigned to two sets Set1 and Set2, so that both sets are equal size. To guarantee the independence of training and testing data, the perturbed polyp images were assigned with their original image into the same set. The cross validation is repeated three times, denoted as Test1, Test2 and Test3. The tests were performed on a standard desktop machine with an Intel Xeon 2.8 GHz CPU and 4 GB RAM. To measure the detection performance, TPR was used at 0.1 FPR. Table 1, shown in FIG. 5, displays a summary of the cross validation performance tests on the original positive images (Original), perturbed images (Perturbed) and combined images (Original+Perturbed), where the overall TPR of Set1 and Set2 for each test is presented at 0.1 FPR. On average, a TPR of 0.637, 0.648 and 0.648 was obtained for the original, perturbed and combined images, respectively. The computation time per image was 0.83±0.26 (mean±standard deviation) second with a median of 0.91 and a maximum of 1.23 second. Note that the training and testing were performed on 27984 images in the computation efficiency test.

System Implementations

It is to be understood that the present disclosure can be implemented in various forms of hardware, software, firmware, special purpose processes, or a combination thereof. In one embodiment, the present disclosure can be implemented in software as an application program tangible embodied on a computer readable program storage device. The application program can be uploaded to, and executed by, a machine comprising any suitable architecture.

Figure 6:
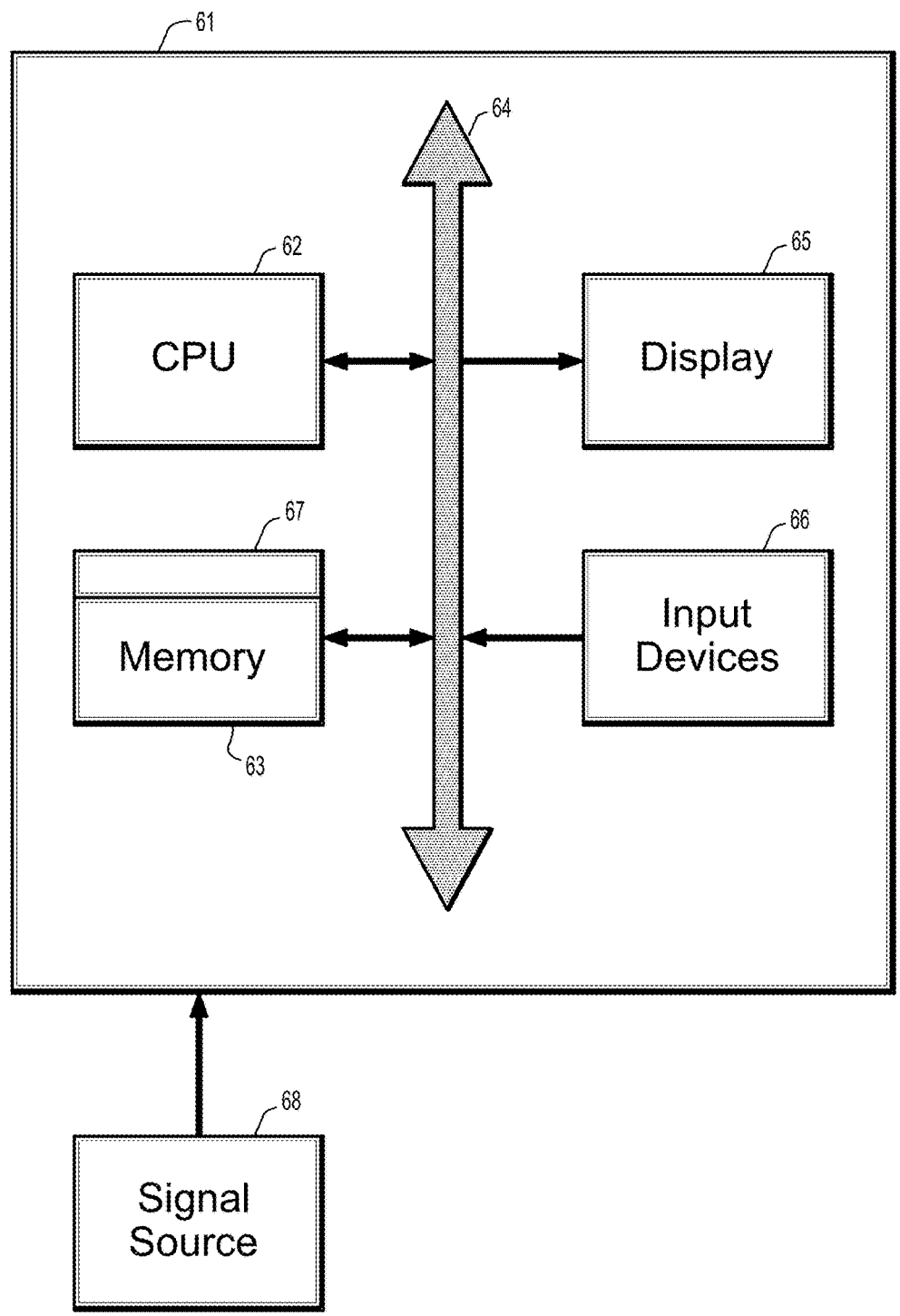
FIG. 6 is a block diagram of an exemplary computer system for implementing a method for detecting polyps in Wireless Capsule Endoscopy (WCE) images, according to an embodiment of the disclosure.

FIG. 6 is a block diagram of an exemplary computer system for implementing a method for detecting polyps in Wireless Capsule Endoscopy (WCE) images according to an embodiment of the disclosure. Referring now to FIG. 6, a computer system 61 for implementing an embodiment of the present disclosure can comprise, inter alia, a central processing unit (CPU) 62, a memory 63 and an input/output (I/O) interface 64. The computer system 61 is generally coupled through the I/O interface 64 to a display 65 and various input devices 66 such as a mouse and a keyboard. The support circuits can include circuits such as cache, power supplies, clock circuits, and a communication bus. The memory 63 can include random access memory (RAM), read only memory (ROM), disk drive, tape drive, etc., or a combinations thereof. Embodiments of the present disclosure can be implemented as a routine 67 that is stored in memory 63 and executed by the CPU 62 to process the signal from the signal source 68. As such, the computer system 61 is a general purpose computer system that becomes a specific purpose computer system when executing the routine 67 of the present disclosure.

The computer system 61 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which an embodiment of the present disclosure is programmed. Given the teachings of embodiments of the present disclosure provided herein, one of ordinary skill in the related art will be able to contemplate these and similar implementations or configurations of the present disclosure.

While embodiments of the present disclosure has been described in detail with reference to exemplary embodiments, those skilled in the art will appreciate that various modifications and substitutions can be made thereto without departing from the spirit and scope of the disclosure as set forth in the appended claims.

What is claimed is:

1. An image processing method for detecting the existence of polyps in endoscopy images obtained from a patient, comprising the steps of, in at least one processor:
receiving a plurality of two dimensional digitized images generated by an endoscopy apparatus;
removing from said plurality of two dimensional digitized images images that are unlikely to depict a polyp, based on results of predefined image-wise processing performed on each of said plurality of two dimensional digitized images, wherein a plurality of candidate images remains that are likely to depict a polyp;
from each of said plurality of candidate images, pruning non-polyp pixels that are unlikely to be part of a polyp depiction, based on results of predefined pixel-wise processing performed on each of said plurality of candidate images;
detecting polyp candidate pixels in the pruned candidate images, based on results of predefined processing performed on pixels of said pruned candidate images;
extracting features from said polyp candidate pixels based on results of predefined processing performed on said polyp candidate pixel;
performing a regression on said extracted features to determine whether said polyp candidate pixels are likely to depict an actual polyp; and
identifying candidate images as depicting polyps based on results of said regression, wherein said identified candidate imaged are used by a clinician to diagnosis a condition of said patient.

2. The method of claim 1, wherein pruning non-polyp pixels from the candidate images comprises calculating a posterior Bayesian probability of a pixel i being a polyp pixel $$g(x_i) \equiv P(x_i \text{ is } polyp) = \frac{P(polyp)f_P(x_i)}{P(polyp)f_P(x_i) + P(\text{normal})f_N(x_i)},$$

wherein $x_i$ is an $N_c$ dimensional vector associated with pixel i that includes intensity values from different color spaces, P(polyp) and P(normal) denote the prior probability that pixel i is a polyp pixel or a non-polyp pixel respectively, and $f_P$ and $f_N$ are distribution functions with respect to $x_i$, given that pixel i is either polyp or non-polyp, respectively, wherein if $g(x_i)$ is less than a predetermined threshold, pixel i is determined to be a non-polyp pixel.

3. The method of claim 2, wherein $N_c = 3$ is a number of color channels, wherein the color channels are (BUH), wherein B is selected from an RGB color space, U is selected from a LUV color space, and H is selected from a HSV color space.

4. The method of claim 2, wherein $g(x_i)$ is approximated by $$\frac{f_P(x_i)}{f_N(x_i)}.$$

5. The method of claim 1, wherein polyp candidates for an image $I_k$ comprise a plurality of ellipses $\{(E_k^l, p_k^l)\}_{l=1}^{N_k}$ for each image $I_k$, wherein ellipse $E_k^l$ is a polyp region-of-interest with a polyp probability $P_k^l$ and $N_k$ is the number of ellipses for image $I_k$.

6. The method of claim 5, wherein features extracted from said polyp candidates include geometric features and appearance based features, wherein said geometric features include an area of each ellipse, and a ratio of the major axis length and the minor axis length of each ellipse, and wherein said appearance based features are extracted from 3 concentric regions-of-interest (ROIs) about the detected ellipse.

7. The method of claim 6, wherein appearance based features include a multi-scaled rotational invariant local binary pattern wherein each of a plurality of circular neighbors of a pixel i are labeled as 1 if the intensity of the neighbor is greater than that of pixel i, and 0 otherwise, and a binary number formed by the values of the plurality of neighbors is classified into a bin based on a number of consecutive 1's and consecutive 0's in each binary number, wherein said binary number is classified into a separate bin if there are no consecutive 1's and consecutive 0's in said binary number, wherein each bin is a feature.

8. The method of claim 6, wherein appearance based features include a histogram of oriented gradients (HOG) calculated by computing image gradients inside each ROI, and assigning a magnitude of each gradient to a direction bin based on an orientation of each polyp candidate ellipse.

9. The method of claim 8, wherein appearance based features further include calculating a dissimilarity of HOG features between two ROIs from $d(f,g) = \sum_{i=1}^{Nf} f_i - g_i$, wherein f and g are HOG histograms for the two regions, respectively, ∥ is an $L_1$ norm, and N is a number of direction bins, and calculating a color distribution dissimilarity between two regions from $d(f,g) = \sum_{i=1}^{N} |f_i - g_i|$, wherein f and g are intensity distribution histograms for the two regions, respectively, for each color.

10. The method of claim 5, wherein performing a regression on said extracted features comprises solving $Y \approx f(X, \beta)$, wherein Y is a target variable, X is a vector of the extracted features, and β are predetermined parameters calculated during a training stage, wherein target value $y_k^l$ for the l-th polyp candidate of image $I_k$ is defined as an overlap ratio between the ellipse $E_k^l$ of the polyp candidate and a ground truth ellipse $E_k^g$ :

$$y_k^l = \begin{cases} \min\left(\frac{|E_k^g \cap E_k^l|}{|E_k^g|}, \frac{|E_k^g \cap E_k^l|}{|E_k^l|}\right) & I_k \text{ is positive image} \\ 0 & I_k \text{ is negative image} \end{cases}$$

wherein ∥ represents an area of the argument ellipse.

11. The method of claim 10, wherein f (X, β) is a support vector regressor.

12. The method of claim 10, further comprising calculating an image-wise polyp score $S_k$ that represents a likelihood that an image $I_k$ contains one or more polyps from $$S_k = \sum_{l=1}^{\tilde{N}_k} (w \cdot p_k^l + (1-w) \cdot y_k^l)$$

wherein $p_k^l$ is the probability of candidate ellipse $E_k^l$ being a polyp wherein $\{p_k^l\}_{l=1}^{N_k}$ is sorted in descending order and a top $\tilde{N}_k$ detected polyp candidates are selected, $y_k^l$ is the corresponding regression target value, and w is a combining weight determined in a training stage to achieve a largest true positive rate at a predetermined false positive rate.

13. A method for training a detector to detect polyps in endoscopy images obtained from a patient, comprising the steps of:

detecting polyp candidates in a plurality of two dimensional digitized images received from an endoscopy apparatus based on results of predefined processing performed on each of said plurality of two dimensional digitized images, such that polyp candidates for an image $I_k$ comprise pixels in a plurality of ellipses $\{(E_k^l, p_k^l)\}_{l=1}^{N_k}$ for each image $I_k$, wherein ellipse $E_k^l$ is a polyp region-of-interest with a polyp probability $p_k^l$ and $N_k$ is the number of ellipses for image $I_k$;

extracting features from said polyp candidates based on results of predefined processing performed on pixels of said polyp candidates;

calculating target values Y for a regression model represented by $Y \approx (X, \beta)$, wherein Y is a target variable characteristic of a polyp candidate depicting an actual polyp, as determined by comparing said extracted features with features for a known actual polyp image, X is a vector of features, and β are unknown parameters to be determined;

determining the parameters β for the regression model from the target values Y and feature vector X; and using the determined parameters β"to train the regression model in said detector".

14. The method of claim 13, wherein target value $y_k^l$ for the l-th polyp candidate of image $I_k$ is defined as an overlap ratio between the ellipse $E_k^l$ of the polyp candidate and a ground truth ellipse $E_k^g$:

$$y_k^l = \begin{cases} \min\left(\frac{|E_k^g \cap E_k^l|}{|E_k^g|}, \frac{|E_k^g \cap E_k^l|}{|E_k^l|}\right) & I_k \text{ is positive image} \\ 0 & I_k \text{ is negative image} \end{cases}$$

wherein ∥ represents an area of the argument ellipse.

15. The method of claim 13, wherein features extracted from said polyp candidates include geometric features and appearance based features, wherein said geometric features include an area of each ellipse, and a ratio of the major axis length and the minor axis length of each ellipse, and wherein said appearance based features are extracted from 3 concentric regions-of-interest (ROIs) about the detected ellipse.

16. The method of claim 15, wherein appearance based features include a multi-scaled rotational invariant local binary pattern wherein each of a plurality of circular neighbors of a pixel i are labeled as 1 if the intensity if the neighbor is greater than that of pixel i, and 0 otherwise, and a binary number formed by the values of the plurality of neighbors is classified into a bin based on a number of consecutive 1's and consecutive 0's in each binary number, wherein said binary number is classified into a separate bin if there are no consecutive 1's and consecutive 0's in said binary number, wherein each bin is a feature.

17. The method of claim 15, wherein appearance based features include a histogram of oriented gradients (HOG) calculated by computing image gradients inside each ROI, and assigning a magnitude of each gradient to a direction bin based on an orientation of each polyp candidate ellipse.

18. The method of claim 15, wherein appearance based features further include calculating a dissimilarity of HOG features between two ROIs from $d(f,g) = \sum_{i=1}^{N} |f_i - g_i|$ wherein f and g are HOG histograms for the two regions, respectively, ∥ is an $L_1$ norm, and N is a number of direction bins, and calculating a color distribution dissimilarity between two regions from $d(f,g) = \sum_{i=1}^{N} |f_i - g_i|$, wherein f and g are intensity distribution histograms for the two regions, respectively, for each color.

19. A non-transitory program storage device readable by a computer, tangibly embodying a program of instructions executed by the computer to detect polyps in endoscopy images obtained from a patient, comprising the steps of:

receiving a plurality of two dimensional digitized images generated by an endoscopy apparatus;

removing from said plurality of two dimensional digitized images images that are unlikely to depict a polyp, based on results of predefined image-wise processing performed on each of said plurality of two dimensional digitized images, wherein a plurality of candidate images remains that are likely to depict a polyp;

from each of said plurality of candidate images, pruning non-polyp pixels that are unlikely to be part of a polyp depiction, based on results of predefined pixel-wise processing performed on each of said plurality of candidate images;

detecting polyp in the pruned candidate images, based on Results of predefined processing performed on pixels of said pruned candidate images;

extracting features from said polyp candidate pixels based on results of predefined predefined processing performed on said polyp candidate pixels;

performing a regression on said extracted features to determine whether said polyp candidate pixels are likely to depict an actual polyp: and identifying candidate images as depicting polyps based on results of said regressinn, wherein said identified candidate imaged are used by a clinician to diagnosis a condition of said patient.

20. The computer readable program storage device of claim 19, wherein pruning non-polyp pixels from the candidate images comprises calculating a posterior Bayesian probability of a pixel i being a polyp pixel $$g(x_i) \equiv P(x_i \text{ is } polyp) = \frac{P(polyp)f_P(x_i)}{P(polyp)f_P(x_i) + P(\text{normal})f_N(x_i)},$$

wherein $x_i$ is an $N_c$ dimensional vector associated with pixel i that includes intensity values from different color spaces, P(polyp) and P(normal) denote the prior probability that pixel i is a polyp pixel or a non-polyp pixel respectively, and $f_p$ and $f_N$ are distribution functions with respect to $x_i$, given that pixel i is either polyp or non-polyp, respectively, wherein if $g(x_i)$ is less than a predetermined threshold, pixel i is determined to be a non-polyp pixel.

21. The computer readable program storage device of claim 20, wherein $N_c$ =3 is a number of color channels, wherein the color channels are (BUH), wherein B is selected from an RGB color space, U is selected from a LUV color space, and H is selected from a HSV color space.

22. The computer readable program storage device of claim 20, wherein $g(x_i)$ is approximated by $$\frac{f_P(x_i)}{f_N(x_i)}.$$

23. The computer readable program storage device of claim 19, wherein polyp candidates for an image $I_k$ comprise a plurality of ellipses $\{(E_k^l, p_k^l)\}_{l=1}^{N_k}$ for each image $I_k$ wherein ellipse $E_k^l$ is a polyp region-of-interest with a polyp probability $p_k^l$ and $N_k$ is the number of ellipses for image $I_k$.

24. The computer readable program storage device of claim 23, wherein features extracted from said polyp candidates include geometric features and appearance based features, wherein said geometric features include an area of each ellipse, and a ratio of the major axis length and the minor axis length of each ellipse, and wherein said appearance based features are extracted from 3 concentric regions-of-interest (ROIs) about the detected ellipse.

25. The computer readable program storage device of claim 24, wherein appearance based features include a multi-scaled rotational invariant local binary pattern wherein each of a plurality of circular neighbors of a pixel i are labeled as 1 if the intensity of the neighbor is greater than that of pixel i, and 0 otherwise, and a binary number formed by the values of the plurality of neighbors is classified into a bin based on a number of consecutive 1's and consecutive 0's in each binary number, wherein said binary number is classified into a separate bin if there are no consecutive 1's and consecutive 0's in said binary number, wherein each bin is a feature.

26. The computer readable program storage device of claim 24, wherein appearance based features include a histogram of oriented gradients (HOG) calculated by computing image gradients inside each ROI, and assigning a magnitude of each gradient to a direction bin based on an orientation of each polyp candidate ellipse.

27. The computer readable program storage device of claim 26, wherein appearance based features further include calculating a dissimilarity of HOG features between two ROIs from $d(f,g)=\Sigma_{i=1}^{N}|g_i-g_i|$, wherein f and g are HOG histograms for the two regions, respectively, ||is an $L_l$ norm, and N is a number of direction bins, and calculating a color distribution dissimilarity between two regions from $d(f,g)=\Sigma_{i=1}^{N}|f_i-g_i|$ wherein f and g are intensity distribution histograms for the two regions, respectively, for each color.

28. The computer readable program storage device of claim 23, wherein performing a regression on said extracted features comprises solving $Y \approx (X,\beta)$, wherein Y is a target variable, X is a vector of the extracted features, and $\beta$ are predetermined parameters calculated during a training stage, wherein target value $y_k^l$ for the l-th polyp candidate of image $I_k$ is defined as an overlap ratio between the ellipse $E_k^l$ of the polyp candidate and a ground truth ellipse $E_k^g$:

$$y_k^l = \begin{cases} \min\left(\frac{|E_k^g \cap E_k^l|}{|E_k^g|}, \frac{|E_k^g \cap E_k^l|}{|E_k^l|}\right) & I_k \text{ is positive image} \\ 0 & I_k \text{ is negative image} \end{cases},$$

wherein ||represents an area of the argument ellipse.

29. The computer readable program storage device of claim 28, wherein $f(X, \beta)$ is a support vector regressor.

30. The computer readable program storage device of claim 28, the method further comprising calculating an image-wise polyp score $S_k$ that represents a likelihood that an image $I_k$ contains one or more polyps from $$S_k = \Sigma_{l=1}^{\tilde{N}_k}(w \cdot p_k^l + (1-W) \cdot y_k^l),$$

wherein $p_k^l$ is the probability of candidate ellipse $E_k^l$ being a polyp wherein $\{p_k^l\}_{l=1}^{N_k}$ is sorted in descending order and a top $\tilde{N}_k$ detected polyp candidates are selected, $y_k^l$ is the corresponding regression target value, and w is a combining weight determined in a training stage to achieve a largest true positive rate at a predetermined false positive rate.

* * * * *